(12) United States Patent  
Djupesland

(10) Patent No.: US 7,543,581 B2
(45) Date of Patent: Jun. 9, 2009

(54) NASAL DEVICES

(75) Inventor: Per Gisle Djupesland, Oslo (NO)

(73) Assignee: OptiNose AS, Olso (NO)

(*) Notice: Subject to any disclaimer, the term of this patent is extended or adjusted under 35 U.S.C. 154(b) by 576 days.

(21) Appl. No.: 10/469,105

(22) PCT Filed: Feb. 26, 2002

(86) PCT No.: PCT/IB02/01521

§ 371 (c)(1),
(2), (4) Date: Mar. 29, 2004

(87) PCT Pub. No.: WO02/068032

PCT Pub. Date: Sep. 6, 2002

(65) Prior Publication Data

US 2004/0149289 A1 Aug. 5, 2004

(51) Int. Cl.
A61M 11/00 (2006.01)
(52) U.S. Cl. ............... 128/200.14; 128/203.12; 128/200.18; 128/200.23; 128/203.15; 128/203.19; 128/203.23
(58) Field of Classification Search ............ 128/203.12, 128/200.18, 200.23, 200.14, 203.15, 203.19, 128/203.23; 222/36, 38, 162
See application file for complete search history.

(56) References Cited

U.S. PATENT DOCUMENTS

| 3,410,264 | A | 11/1968 | Frederick |
| 5,335,656 | A | 8/1994 | Bowe et al. |
| 5,531,218 | A | 7/1996 | Krebs |
| 5,743,256 | A | 4/1998 | Jalowayski |
| 6,155,986 | A | 12/2000 | Brydon et al. |

FOREIGN PATENT DOCUMENTS

| EP | 0 824 023 | | 8/1998 |
| FR | 2 370 461 | | 6/1978 |
| GB | 814160 | | 5/1959 |
| GB | 1 342 370 | | 1/1974 |
| WO | 00/06020 | | 2/2000 |
| WO | 00/51672 | | 9/2000 |
| WO | WO 00/51672 | * | 9/2000 |

* cited by examiner

Primary Examiner—Patricia M Bianco
Assistant Examiner—Nihir Patel
(74) Attorney, Agent, or Firm—Proskauer Rose LLP; Kristin H. Neuman, Esq.; Issac A. Hubner

(57) ABSTRACT

A nasal delivery device for and a method of delivering at least one substance to a nasal cavity of a subject. The nasal delivery device and method includes a delivery unit comprising: a nosepiece for fitting to a nostril of a subject; a mouthpiece through which the subject in use exhales; a breath analyzer for analyzing the concentration of at least one component in exhaled air from an exhalation breath; and a substance supply unit for supply at least one substance, the substance supply unit including a control unit for controlling the same to control supply of at least one substance in response to the detected concentration.

43 Claims, 4 Drawing Sheets

NASAL DEVICES

This application is a national phase of International Application No. PCT/IB02/01521 filed Feb. 26, 2002 and published in the English language.

FIELD OF THE INVENTION

The present invention relates to a nasal delivery device for and a method of delivering a substance, in particular one of a liquid, as a suspension or solution, or a powder containing a medicament, especially systemic or topical pharmaceuticals, to the nasal airway of a subject, and a nasal resistance measurement device for and a method of determining nasal resistances of nasal airways of subjects.

BACKGROUND OF THE INVENTION

Referring to FIG. 1, the nasal airway 1 comprises the two nasal cavities 2, 3 separated by the nasal septum 4, which airway 1 includes numerous ostia, such as the paranasal sinus ostia 5 connected to the paranasal sinuses 6 and the tubal ostia 7 connected to the tuba auditiva 8 and the middle ears 9, and olfactory cells, and is lined by the nasal mucosa The nasal airway 1 can communicate with the nasopharynx, the oral cavity and the lower airway, with the nasal airway 1 being in selective communication with the anterior region of the nasopharynx and the oral cavity by opening and closing of the oropharyngeal velum.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitionin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as helicobacter pylori infections which cause gastric ulcers.

WO-A-00/51672 discloses a delivery device for delivering a substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

SUMMARY OF THE INVENTION

In one aspect the present invention provides a nasal delivery device for delivering at least one substance to a nasal cavity of a subject, including a delivery unit comprising: a nosepiece for fitting to a nostril of a subject; a mouthpiece through which the subject in use exhales; a breath analyzer for analyzing the concentration of at least one component in exhaled air from an exhalation breath; and a substance supply unit for supplying at least one substance, the substance supply unit including a control unit for controlling the same to control supply of the at least one substance in response to the detected concentration.

In one embodiment the control unit is configured to actuate the substance supply unit to supply the at least one substance at a predeterminable pressure.

In another embodiment the control unit is configured to actuate the substance supply unit to supply the at least one substance at a predeterminable flow rate.

In a further embodiment the control unit is configured to actuate the substance supply unit to supply the at least one substance at one or both of a predeterminable pressure and a predeterminable flow rate.

In one embodiment the delivery unit further comprises: a flow channel fluidly connecting the nosepiece and the mouthpiece, whereby exhaled air from an exhalation breath is delivered through the nosepiece.

Preferably, the substance supply unit includes a flow regulator for regulating the exhaled air flow.

More preferably, the flow regulator is operably coupled to the control unit such as to allow for control of the same.

In another embodiment the delivery unit further comprises: a flow channel fluidly connected to the nosepiece through which a gas flow, separate to an exhaled air flow from an exhalation breath of a subject, is in use delivered; and a gas supply unit for supplying a gas flow to the flow channel.

Preferably, the substance supply unit includes a dosing unit for supplying at least one substance.

In one embodiment the dosing unit comprises a nebulizer for supplying an aerosol.

In another embodiment the dosing unit comprises an aerosol canister for supplying an aerosol.

In a further embodiment the dosing unit comprises a delivery pump unit for supplying an aerosol.

In one preferred embodiment the dosing unit comprises a liquid pump unit for supplying a liquid aerosol.

In another preferred embodiment the dosing unit comprises a powder pump unit for supplying a powder aerosol.

In a still yet further embodiment the dosing unit comprises a powder delivery unit for delivering a powder aerosol.

Preferably, the delivery device further includes an outlet unit comprising: a nosepiece for fitting in the other, outlet nostril of the subject; and an exit flow analyzer for analyzing the concentration of at least one component in an air flow exiting the outlet nostril.

More preferably, the exit flow analyzer is operably connected to the control unit, and the control unit is configured to control the substance supply unit in response to a concentration detected by the exit flow analyzer.

In another aspect the present invention provides a method of delivering at least one substance to a nasal cavity of a subject, comprising the steps of: providing a delivery device including a delivery unit comprising a nosepiece for fitting to a nostril of a subject, a mouthpiece through which the subject exhales, a breath analyzer for analyzing the concentration of at least one component in exhaled air from an exhalation breath, and a substance supply unit for supplying at least one substance; actuating the substance supply unit to supply at least one substance; and controlling supply of the at least one substance by the substance supply unit in response to concentration as detected by the breath analyzer.

In one embodiment the step of actuating the substance supply unit comprises the step of: actuating the substance supply unit to supply the at least one substance at a predeterminable pressure.

In another embodiment the step of actuating the substance supply unit comprises the step of: actuating the substance supply unit to supply the at least one substance at a predeterminable flow rate.

In a further embodiment the step of actuating the substance supply unit comprises the step of: actuating the substance supply unit to supply the at least one substance at one or both of a predeterminable pressure and a predeterminable flow rate.

In one embodiment the delivery unit further comprises: a flow channel fluidly connecting the nosepiece and the mouthpiece, whereby exhaled air from an exhalation breath is delivered through the nosepiece.

Preferably, the method further comprises the step of: regulating the exhaled air flow.

In another embodiment the method further comprises the step of: delivering a gas flow, separate to an exhaled air flow from an exhalation breath of a subject, through the nosepiece.

Preferably, the substance supply unit includes a dosing unit for supplying at least one substance.

In one embodiment the dosing unit comprises a nebulizer for supplying an aerosol.

In another embodiment the dosing unit comprises an aerosol canister for supplying an aerosol.

In a further embodiment the dosing unit comprises a delivery pump unit for supplying an aerosol.

In one preferred embodiment the dosing unit comprises a liquid pump unit for supplying a liquid aerosol.

In another preferred embodiment the dosing unit comprises a powder pump unit for supplying a powder aerosol.

In a yet further embodiment the dosing unit comprises a powder delivery unit for delivering a powder aerosol.

Preferably, the delivery device further includes an outlet unit comprising a nosepiece for fitting in the other, outlet nostril of the subject, and an exit flow analyzer for analyzing the concentration of at least one component in an air flow exiting the outlet nostril.

More preferably, the method further comprises the step of: controlling the substance supply unit in response to a concentration as detected by the exit flow analyzer.

Preferably, the step of controlling the substance supply unit in response to a concentration as detected by the exit flow analyzer comprises the step of: actuating the substance supply unit to supply further of the at least one substance in response to detection of a concentration of the at least one substance by the exit flow analyzer.

Preferably, the step of controlling the substance supply unit in response to a concentration as detected by the exit flow analyzer comprises the step of: actuating the substance supply unit to supply a reference substance; and controlling the substance supply unit in response to a concentration of the reference substance as detected by the exit flow analyzer.

In a further aspect the present invention provides a nasal delivery device for delivering at least one substance to a nasal cavity of a subject, comprising: a flow channel including a mouthpiece through which a subject exhales and a nosepiece for fitting to one nostril of the subject and through which the exhaled air flow is delivered to the nostril of the subject; a breath analyzer for analysing the concentration of at least one component in the exhaled air flow; and a substance supply unit for supplying at least one substance to the exhaled air flow, the substance supply unit including a control unit for controlling the same to meter the supply of the at least one substance in response to the detected concentration.

In a yet further aspect the present invention provides a nasal resistance measurement device for determining a flow resistance of a nasal airway of a subject, comprising: a nosepiece for fitting to a nostril of a subject; a mouthpiece through which the subject in use exhales; and one or both of a pressure detector for detecting a pressure and a flow meter for detecting a flow rate of a gas flow delivered through the nosepiece.

In one embodiment the measurement device comprises: a pressure detector for detecting a pressure of a gas flow delivered through the nosepiece.

In another embodiment the measurement device comprises: a flow meter for detecting a flow rate of a gas flow delivered through the nosepiece.

In a further embodiment the measurement device comprises: a pressure detector for detecting a pressure of a gas flow delivered through the nosepiece; and a flow meter for detecting a flow rate of a gas flow delivered through the nosepiece.

In one embodiment the pressure detector comprises a mechanical pressure detector.

In another embodiment the pressure detector comprises an electronic pressure detector.

In one embodiment the flow meter comprises a mechanical flow meter.

In a further embodiment the flow meter comprises an electronic flow meter.

In one embodiment the nosepiece comprises a frusto-conical nosepiece for insertion into a nostril.

In a further embodiment the nosepiece comprises a sealing ring for fitting externally to a nostril.

Preferably, the measurement device further comprises: a determination unit for determining a nasal resistance from one or both of a pressure and flow rate as detected.

In one embodiment the measurement device further comprises: a flow channel fluidly connecting the nosepiece and the mouthpiece, whereby exhaled air from an exhalation breath is delivered through the nosepiece.

Preferably, the measurement device further comprises: a flow regulator for regulating the exhaled air flow.

In another embodiment the measurement device further comprises: a flow channel fluidly connected to the nosepiece through which a gas flow, separate to an exhaled air flow from an exhalation breath of a subject, is in use delivered; and a gas supply unit for supplying a gas flow to the flow channel.

In yet another aspect the present invention provides a nasal resistance measurement device for determining a flow resistance of a nasal airway of a subject, comprising: a flow channel including a mouthpiece through which a subject in use exhales and a nosepiece for fitting to one nostril of the subject and through which the exhaled air flow is in use delivered to the nostril of the subject; and a flow meter and/or pressure gauge for measuring the flow and/or pressure of the exhaled air flow.

In still yet another aspect the present invention provides a method of determining a flow resistance of a nasal airway of a subject, comprising the steps of: providing a measurement device comprising a nosepiece for fitting to a nostril of a subject, and a mouthpiece through which the subject exhales; and detecting one or both of a pressure and a flow rate of a gas flow delivered through the nosepiece during exhalation through the mouthpiece by the subject.

In one embodiment the step of detecting one or both of a pressure and a flow rate of a gas flow delivered through the nosepiece comprises the step of: detecting a pressure of a gas flow delivered through the nosepiece.

In another embodiment the step of detecting one or both of a pressure and a flow rate of a gas flow delivered through the nosepiece comprises the step of: detecting a flow rate of a gas flow delivered through the nosepiece.

In a further embodiment the step of detecting one or both of a pressure and a flow rate of a gas flow delivered through the nosepiece comprises the step of: detecting a pressure and a flow rate of a gas flow delivered through the nosepiece.

In one embodiment the nosepiece comprises a frusto-conical nosepiece for insertion into a nostril.

In another embodiment the nosepiece comprises a sealing ring for fitting externally to a nostril.

Preferably, the method further comprises the step of: determining a nasal resistance from one or both of a pressure and flow rate as detected.

In one embodiment the measurement device further comprises: a flow channel fluidly connecting the nosepiece and the mouthpiece, whereby exhaled air from an exhalation breath is delivered through the nosepiece.

Preferably, the method further comprises the step of: regulating a flow rate of an exhaled air flow.

In another embodiment the method further comprises the step of: delivering a gas flow, separate to an exhaled air flow from an exhalation breath of a subject, through the nosepiece.

BRIEF DESCRIPTION OF THE DRAWINGS

Preferred embodiments of the present invention will now be described hereinbelow by way of example only with reference to the accompanying drawings, in which.

DETAILED DESCRIPTION OF THE INVENTION

Figure 2:
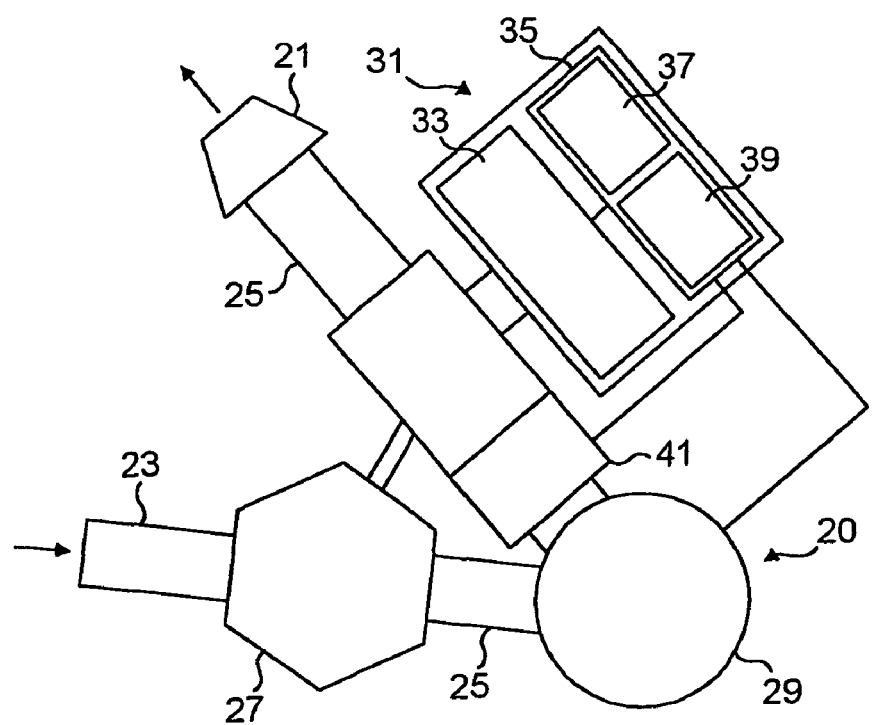
FIG. 2 schematically illustrates a nasal delivery device in accordance with a first embodiment of the present invention.

FIG. 2 illustrates a nasal delivery device in accordance with a first embodiment of the present invention. The delivery device comprises a delivery unit 20 for delivering a metered dose of at least one substance in response to the detected concentration of at least one component in an exhalation breath of a subject.

The delivery unit 20 comprises a nosepiece 21 for fitting in one nostril of a subject to provide a fluid-tight seal therewith, a mouthpiece 23 through which the subject exhales, and a flow channel 25 fluidly connecting the nosepiece 21 and the mouthpiece 23. With this configuration, exhaled air from the exhalation breath of a subject is delivered through the nasal airway of the subject.

In this embodiment the delivery unit 20 further comprises a filter unit 27 which is disposed at the inlet end of the flow channel 25, here including a moisture filter. In a preferred embodiment the filter unit 27 could include an anti-microbial filter.

The delivery unit 20 further comprises a breath analyzer 29, in this embodiment disposed downstream of the filter unit 27, for detecting the concentration of at least one component in exhaled air from an exhalation breath. In a preferred embodiment the breath analyser 29 is configured to detect the concentration of a plurality of components in exhaled air from an exhalation breath.

The delivery unit 20 further comprises a substance supply unit 31 which is operably coupled to the breath analyzer 29 for dosing at least one substance to the flow channel 25 in response to the concentration of the at least one component as detected by the breath analyzer 29, such as to be entrained by the exhaled air flow from an exhalation breath of a subject and delivered through the nasal airway of the subject. In this embodiment the substance supply unit 31 is fluidly connected to the flow channel 25 downstream of the breath analyzer 29.

The substance supply unit 31 comprises a dosing unit 33 for dosing at least one substance to the flow channel 25, and a control unit 35 connected to the breath analyzer 29 for actuating the dosing unit 33 to deliver a metered dose of at least one substance in response to the concentration of the at least one component as detected by the breath analyzer 29.

In this embodiment the dosing unit 33 is configured to be actuatable to deliver aerosols having different particle size distributions, whereby an aerosol can be delivered having a desired particle size distribution.

In this embodiment the dosing unit 33 comprises a nebulizer for delivering metered amounts of a substance, as an aerosol, on actuation thereof. In this embodiment control of the particle size distribution of the aerosol is effected by controlling the aerosol generator.

In this embodiment the nebulizer comprises an ultrasonic nebulizer, whereby a liquid aerosol is generated by the vibration of a liquid supply, here a liquid containing a medicament, either as a solution or suspension, at a predetermined frequency, typically utilizing a piezo-electric element, with the frequency determining the particle size distribution of the delivered aerosol.

In another embodiment the nebulizer could comprise a flow-induced nebulizer, whereby a gas flow interacts with a liquid supplied from a nozzle to generate a liquid aerosol, with the flow rate and the nozzle geometry determining the particle size distribution of the delivered aerosol.

In another embodiment the nebulizer could comprise an electrohydrodynamic (EHD) nebulizer, such nebulizers being capable of generating aerosols from liquid solutions or suspensions. In this nebulizer, flows of liquid are charged by an electric field, which charge builds up on the liquid surface, such that, when the liquid flows exit the respective nozzles, the repelling force of the surface charge overcomes the surface tension of the liquid and develops a fine aerosol. The particle size distribution of the aerosol can be controlled by adjusting a number of variables, such as physical and chemical properties of the drug formulations, the operating conditions, and the electric field.

In an alternative embodiment the dosing unit 33 could comprise an actuatable aerosol canister, here mechanically-operable or electrically-operable, for delivering metered amounts of a substance contained, either as a suspension or a solution, in a propellant, preferably a hydrofluoroalkane (HFA) propellant or the like, as an aerosol, on actuation thereof. In this embodiment control of the particle size distribution of the aerosol is effected by controlling the configuration, typically the aperture, of the nozzle block.

In another alternative embodiment the dosing unit 33 could comprise an actuatable spray pump unit, here mechanically-operable or electrically-operable, for delivering metered amounts of a substance as a liquid aerosol on actuation thereof. In this embodiment control of the particle size distribution of the aerosol is effected by controlling the configuration, typically the aperture, of the nozzle block.

In yet another alternative embodiment the dosing unit 33 could comprise an actuatable dry powder delivery unit, here mechanically-operable or electrically-operable, which delivers metered amounts of a substance, as a dry powder aerosol, on actuation thereof. In this embodiment control of the particle size distribution of the aerosol can be effected by controlling the operation of the particle de-agglomerator.

The control unit 35 comprises a characterization unit 37, in this embodiment utilizing a plurality of look-up tables, for characterizing exhaled air from an exhalation breath from the concentration of the at least one component therein, and a determination unit 39 for determining the dosing characteristics of the dose of substance to be delivered in accordance with the characterization. By characterizing the exhaled air, the delivered aerosol can be delivered with optimal dosing characteristics for treatment of the characterized condition.

The control unit 35 further comprises a flow regulator 41 for regulating the exhaled air flow delivered through the nosepiece 21. By the provision of the flow regulator 41, the flow rate of the air delivered through the nasal airway of a subject can be controlled.

In this embodiment the control unit 35 is configured to actuate the dosing unit 33 to deliver a metered dose of at least one substance in a single delivery. In an alternative embodiment the control unit 35 could be configured to actuate the dosing unit 33 to deliver a metered dose of at least one substance in a plurality of successive deliveries, that is, as a plurality of bursts, during the exhalation breath of a subject, whereby a prolonged delivery can be achieved.

Operation of the nasal delivery device will now be described hereinbelow.

Firstly, a subject fits the nosepiece 21 to one nostril and grips the mouthpiece 23 in the mouth. The subject then exhales through the mouthpiece 23 such as to deliver an exhaled air flow from the exhalation breath through the flow channel 25 and the nasal airway of the subject. The exhaled air flow is first filtered by the filter unit 27, and then the concentration of at least one component in the exhaled air is detected by the breath analyzer 29. The control unit 35 of the substance supply unit 31 acts to characterize the exhaled air and determine the optimal dosing characteristics, namely the delivery regime, including the amount of the dose, the particle size distribution of the delivered aerosol and the delivery flow rate.

In one mode of use, the control unit 35 is configured to actuate the dosing unit 33 and the flow regulator 41 instantly in the same exhalation breath to deliver an aerosol entrained in the instant exhaled air flow as optimized in accordance with the dosing characteristics. This on-line characterization and determination is particularly suited to the treatment of conditions which are relatively highly time variant and dose dependent.

In another mode of use, the control unit 35 is configured to actuate the dosing unit 33 and the flow regulator 41 in accordance with the dosing characteristics as determined in the previous exhalation breath to deliver an aerosol entrained in the instant air flow as optimized in accordance with the previously-determined dosing characteristics. This mode of use is particularly suited to applications where relatively frequent use of the delivery device is required, and a short delay in delivering substance in accordance with the modified dosing characteristics corresponding to the delivery interval is not particularly significant. In allowing the control unit 35 to perform the characterization and determination off-line, more refined characterization and determination can be performed as compared to on-line characterization and determination.

The exhaled breath of any subject represents a mirror of the metabolic processes in the body. In the alveoli of the lungs the thinnest barrier between the blood and the inhaled/exhaled air is found. Changes in the blood will be reflected in the composition of the exhaled breath. Breath analyzers are already available, and diagnostic techniques are constantly improving. In a preferred embodiment, by combining breath analysis with bi-directional nasal drug delivery, an on-line output-input system is achieved utilizing breath analysis as a diagnostic tool. For example, the metabolic status for chronic diseases, such as diabetes, can be monitored by the analysis of exhaled breath, in the same manner as samples of blood or urine are used currently. The separation of the lower airway and the nasal airway during velum closure, and the attainment of bi-directional nasal air flow, provide a system for breath analysis and the delivery of a correct dose of medicament, such as systemic drugs like insulin, to the nasal airway.

Figure 3:
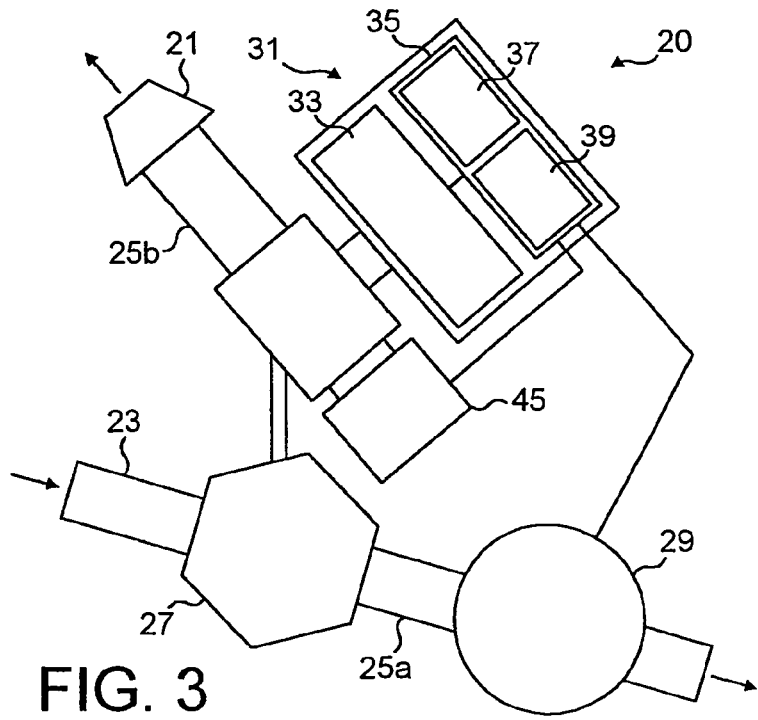
FIG. 3 schematically illustrates a nasal delivery device in accordance with a second embodiment of the present invention.

FIG. 3 illustrates a nasal delivery device in accordance with a second embodiment of the present invention.

The nasal delivery device of this embodiment is very similar to the nasal delivery device of the above-described first embodiment, and thus, in order to avoid unnecessary duplication of description, only the differences will be described in detail, with like reference signs designating like parts The nasal delivery unit 20 of this embodiment differs from that of the above-described first embodiment only in that the flow channel 25 comprises first and second flow channel sections 25a, 25b which are not in fluid communication, and in that the substance supply unit 31 includes a regulatable gas supply unit 45 which is fluidly connected to the second flow channel section 25b in place of the flow regulator 41 for delivering a controlled gas flow through the second flow channel section 25b, and hence the nasal airway of a subject. In this embodiment the control unit 35 is configured to enable actuation of the dosing unit 33 only on receipt of an output signal from the breath analyzer 29; this signal being indicative that the subject is still exhaling through the mouthpiece 23, which exhalation acts to close the oropharyngeal velum of the subject, and thereby prevent delivery to the lower airway and ensure bi-directional delivery through the nasal cavities around the nasal septum.

Operation of the delivery device is substantially the same as for the delivery device of the above-described first embodiment, with the only difference being that the delivered gas flow is not the exhaled air from an exhalation breath of a subject, but delivered separately from the separate gas supply unit 45.

Figure 4:
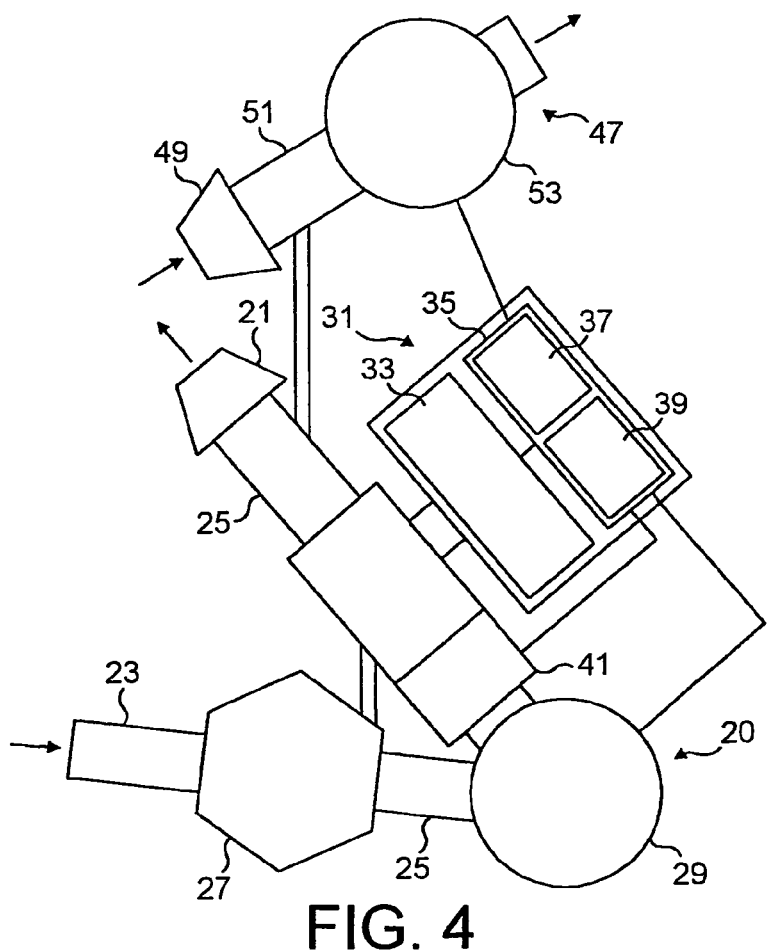
FIG. 4 schematically illustrates a nasal delivery device in accordance with a third embodiment of the present invention.

FIG. 4 illustrates a nasal delivery device in accordance with a third embodiment of the present invention.

The nasal delivery device of this embodiment is very similar to the nasal delivery device of the above-described first embodiment, and thus, in order to avoid unnecessary duplication of description, only the differences will be described in detail, with like reference signs designating like parts The nasal delivery unit 20 of this embodiment differs from that of the above-described first embodiment in further comprising an outlet unit 47 for fitting to the other nostril of a subject to which the delivery unit 20 is fitted.

The outlet unit 47 comprises a nosepiece 49 for fitting in the other, exit nostril of a subject to provide a fluid-tight seal therewith, a flow channel 51 which is fluidly connected to the nosepiece 49, and an exit flow analyzer 53 for detecting the concentration of at least one substance, in particular the delivered substance, which escapes from the exit nostril. In this embodiment the outlet unit 47 is fixedly connected to the delivery unit 20 such as to provide for three-point fixation of the delivery device, with the points of fixation being at the mouthpiece 23 and the nosepieces 21, 49. In this way, the delivery device is repeatedly used correctly to deliver substance to the nasal airway. In an alternative embodiment the outlet unit 47 could be separate from the delivery unit 20 or connected by a loose connection.

The nasal delivery unit 20 of this embodiment differs from that of the above-described first embodiment further only in that the control unit 35 of the substance supply unit 31 is operably connected to the exit flow analyzer 53 such as to enable actuation of the dosing unit 33 in response to the concentration of at least one component detected by the exit flow analyzer 53, in particular to deliver an increased dose of substance to accommodate the amount of substance which escapes from the nasal airway through the exit nostril.

Operation of the delivery device is the same as for the delivery device of the above-described first embodiment, with the feedback from the exit flow analyzer 53 allowing for the dosing unit 33 to deliver a further, additional dose of substance to accommodate the amount of substance which escapes from the nasal airway through the exit nostril.

In one embodiment the dosing unit 33 can provide for the delivery of an aerosol of a reference substance to the flow channel 25, and the exit flow analyzer 53 provides for the detection of the concentration of the substance which escapes from the exit nostril. In this way, the delivery device provides for a testing function, whereby the patency and resistance of the nasal airway can be determined prior to delivery of active substance, with the dosing unit 33 being configured to deliver substance with dosing characteristics responsive to the concentration of at least one component detected by the exit flow analyzer 53.

Figure 5:
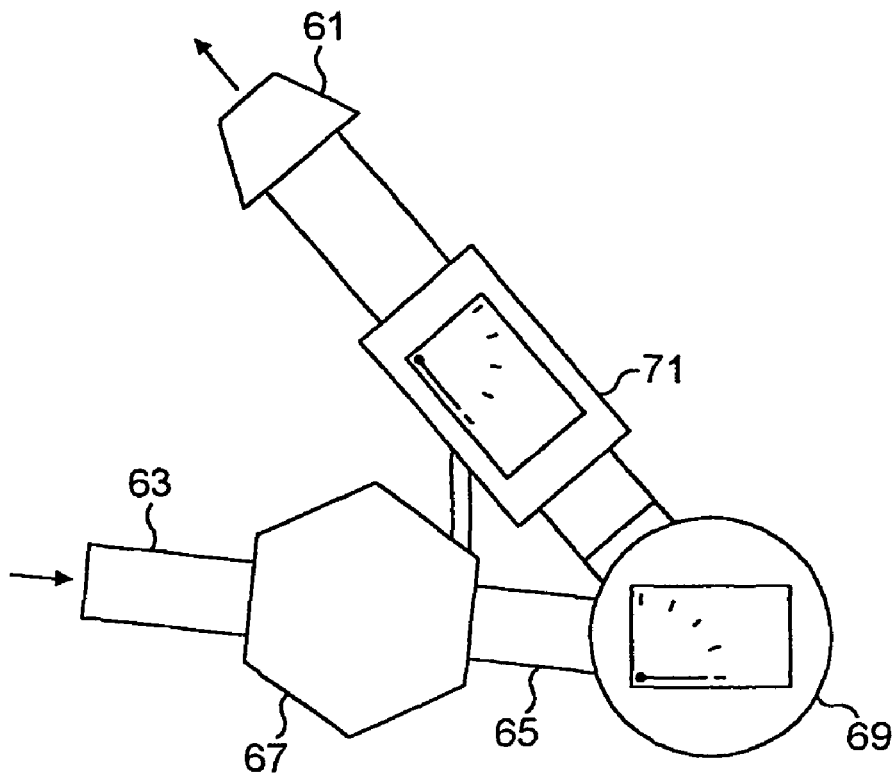
FIG. 5 schematically illustrates a nasal resistance measurement device in accordance with a fourth embodiment of the present invention.

FIG. 5 illustrates a nasal resistance measurement device for determining nasal resistance in accordance with a fourth embodiment of the present invention.

The measurement device comprises a nosepiece 61 for fitting in one nostril of a subject to provide a fluid-tight seal therewith, a mouthpiece 63 through which the subject exhales, and a flow channel 65 which fluidly connects the nosepiece 61 and the mouthpiece 63. With this configuration, exhaled air from an exhalation breath of a subject is delivered through the nasal airway of a subject.

In this embodiment the nosepiece 61 is a nosepiece of predetermined shape and configuration which is used as a reference nosepiece in determining nasal resistance. It will be understood that the nosepiece 61, when inserted in a nostril, will expand the nasal cavity of that nostril and thus to some extent cause the measured nasal resistance to be to some extent lower than the actual nasal resistance.

Figure 6:
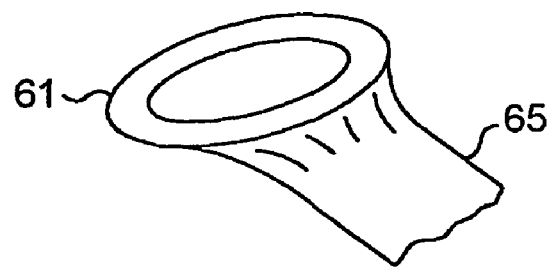
FIG. 6 illustrates an alternative nosepiece for the measurement device of FIG. 5.

In an alternative embodiment, as illustrated in FIG. 6, the nosepiece 61 comprises an anatomical adaptor, typically in the form of a sealing ring, which provides a fluid-tight seal with the nares of the nostril. By the use of such a nosepiece 61, the nasal cavity is not expanded, such that the measured resistance is the actual nasal resistance. In a preferred embodiment the nosepiece 61 could be a replaceable element. In one embodiment the nosepiece 61 includes an adhesive surface for adhesion to the nares of the nostril.

In this embodiment the measurement device further comprises a filter unit 67 which is disposed at the inlet end of the flow channel 65, here including a moisture filter. In a preferred embodiment the filter unit 67 could include an anti-microbial filter.

The measurement device further comprises a pressure detector 69, in this embodiment a mechanical pressure detector having a gauge for recording the peak pressure developed, which is disposed in the flow channel 65, in this embodiment downstream of the filter unit 67, for detecting the pressure developed in the flow channel 65 on exhalation by the subject therethrough.

The measurement device further comprises a flow meter 71, in this embodiment a mechanical flow meter of the rotameter type which includes a gauge for recording the peak flow rate developed, which is disposed in the flow channel 65, in this embodiment downstream of the filter unit 67, for detecting the flow rate in the flow channel 65 on exhalation by the subject therethrough.

Figure 1:
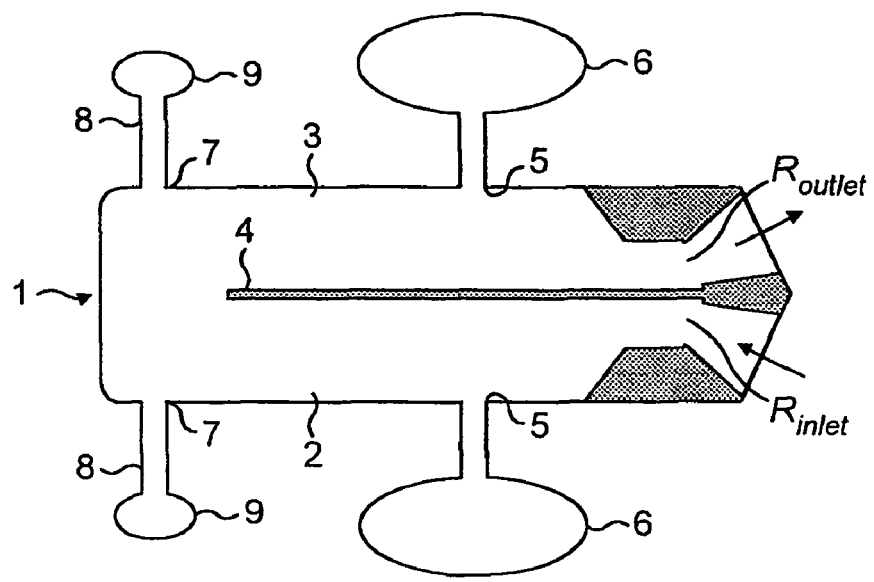
FIG. 1 schematically illustrates the nasal airway of a human subject.

Operation of the delivery device will now be described hereinbelow with reference to FIG. 1, which drawing diagrammatically illustrates the nasal airway 1 of a human subject.

A subject fits the nosepiece 61 to one nostril and grips the mouthpiece 63 in the mouth. The subject then exhales through the mouthpiece 63 such as to deliver an exhaled air flow from an exhalation breath through the flow channel 65 and the nasal airway 1 of the subject, with the exhaled air flow being first filtered by the filter unit 67.

The peak pressure developed in the flow channel 65 is recorded by the pressure detector 69 and the peak flow rate in the flow channel 65 is recorded by the flow meter 71.

The pressure P and flow rate F are related to the nasal resistance R, which is the in series resistance of the inlet nasal cavity $R_{inlet}$ and the outlet nasal cavity $R_{outlet}$, by the equation R=F/P. The nasal resistance R is thus determined from the measured values of pressure P and flow rate F.

Figure 7:
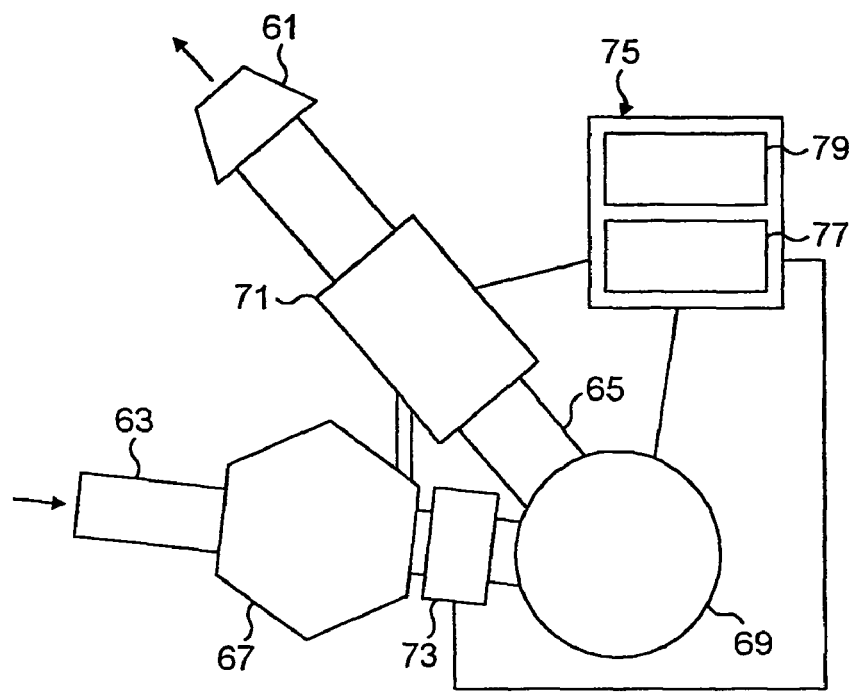
FIG. 7 schematically illustrates a nasal resistance measurement device in accordance with a fifth embodiment of the present invention.

FIG. 7 illustrates a nasal resistance measurement device for determining nasal resistance in accordance with a fifth embodiment of the present invention.

The measurement device comprises a nosepiece 61 for fitting in one nostril of a subject to provide a fluid-tight seal therewith, a mouthpiece 63 through which the subject exhales, and a flow channel 65 which fluidly connects the nosepiece 61 and the mouthpiece 63. With this configuration, exhaled air from an exhalation breath of a subject is delivered through the nasal airway of the subject.

In this embodiment the nosepiece 61 is a nosepiece of predetermined shape and configuration which is used as a reference nosepiece in determining nasal resistance. It will be understood that the nosepiece 61, when inserted in a nostril, will expand the nasal cavity of that nostril and thus to some extent cause the measured nasal resistance to be to some extent lower than the actual nasal resistance.

In an alternative embodiment, as illustrated in FIG. 6, the nosepiece 61 comprises an anatomical adaptor, typically in the form of a sealing ring, which provides a fluid-tight seal with the nares of the nostril. By the use of such a nosepiece 61, the nasal cavity is not expanded, such that the measured resistance is the actual nasal resistance.

In this embodiment the measurement device further comprises a filter unit 67 which is disposed at the inlet end of the flow channel 65, here including a moisture filter. In a preferred embodiment the filter unit 67 could include an anti-microbial filter.

The measurement device further comprises a pressure detector 69, in this embodiment an electronic pressure detector for recording the pressure developed, which is disposed in the flow channel 65, in this embodiment downstream of the filter unit 67, for detecting the pressure developed in the flow channel 65 on exhalation by the subject therethrough.

The measurement device further comprises a flow meter 71, in this embodiment an electronic flow meter for recording the flow rate developed, which is disposed in the flow channel 65, in this embodiment downstream of the filter unit 67, for detecting the flow rate in the flow channel 65 on exhalation by the subject therethrough.

The measurement device further comprises a flow regulator 73 which is disposed upstream of the pressure sensor 69 and is actuatable to control the flow rate of the exhaled air flow. In this embodiment the flow regulator 73 includes an electrically-operable baffle which is movable in the flow channel 65 to restrict the flow therethrough and thereby enable control of the flow rate to predeterminable values.

The measurement device further comprises a determination unit 75 which is operably coupled to the pressure sensor 69, the flow meter 71 and the flow regulator 73.

The determination unit 75 includes a calculation unit 77 for calculating the nasal resistance R from the pressure P detected by the pressure sensor 69 and the flow rate F detected by the flow meter 71 for predetermined flow rates as set by the flow regulator 73. The pressure P and flow rate F are related to the nasal resistance R, which is the in-series resistance of the inlet nasal cavity $R_{inlet}$ and the outlet nasal cavity $R_{outlet}$, by the equation R=F/P. The nasal resistance R is thus determined from the measured values of pressure P and flow rate F.

The determination unit 75 further comprises a display 79 for displaying the determined resistance values.

In an alternative embodiment the determination unit can include a communications port for communicating with a personal computer (PC) to allow downloading of the acquired data.

Operation of the delivery device will now be described hereinbelow.

A subject fits the nosepiece 61 to one nostril and grips the mouthpiece 63 in the mouth. The subject then exhales through the mouthpiece 63 such as to deliver the air flow from the exhalation breath through the flow channel 65 and the nasal airway of the subject, with the exhaled air flow being first filtered by the filter unit 67.

In one mode of operation, in a single exhalation breath, the determination unit 75 actuates the flow regulator 73 to limit the flow rate to a predetermined flow rate, and determines the nasal resistance R for the detected values of pressure P and flow rate F, with the determined nasal resistance R being displayed on the display 79. In this mode, the nasal resistances R are determined for other flow rates F by repeated exhalation through the mouthpiece 63.

In another mode of operation, in a single exhalation breath, the determination unit 75 actuates the flow regulator 73 to limit the flow rate successively to a plurality of different predetermined flow rates, and determines the nasal resistance R for the detected values of pressure P and flow rate F, with the determined nasal resistance R being displayed on the display 79.

Figure 8:
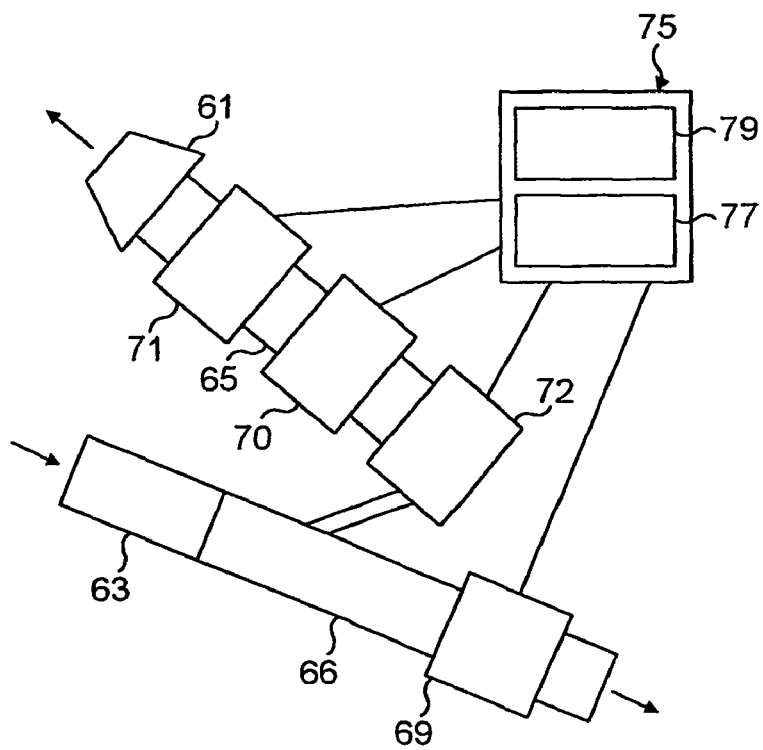
FIG. 8 schematically illustrates a nasal resistance measurement device in accordance with a sixth embodiment of the present invention.

FIG. 8 illustrates a nasal resistance measurement device for determining nasal resistance in accordance with a sixth embodiment of the present invention.

The measurement device comprises a nosepiece 61 for fitting in one nostril of a subject to provide a fluid-tight seal therewith, a mouthpiece 63 through which the subject exhales, and a first flow channel 65 is fluidly connected to the nosepiece 61, and a second flow channel 66 which is fluidly connected to the mouthpiece 63.

In this embodiment the nosepiece 61 is a nosepiece of predetermined shape and configuration which is used as a reference nosepiece in determining nasal resistance. It will be understood that the nosepiece 61, when inserted in a nostril, will expand the nasal cavity of that nostril and thus to some extent cause the measured nasal resistance to be to some extent lower than the actual nasal resistance.

In an alternative embodiment, as illustrated in FIG. 6, the nosepiece 61 comprises an anatomical adaptor, typically in the form of a sealing ring, which provides a fluid-tight seal with the nares of the nostril. By the use of such a nosepiece 61, the nasal cavity is not expanded, such that the measured resistance is the actual nasal resistance.

The measurement device further comprises a first pressure detector 69, in this embodiment an electronic pressure detector, which is disposed in the second flow channel 66 for detecting the presence of a predetermined pressure in the second flow channel 66 on exhalation by the subject therethrough; this pressure being indicative of the maintenance of an exhalation flow which is such as to maintain the oropharyngeal velum in the closed position, as is necessary for a bi-directional flow through the nasal cavities of a subject.

The measurement device further comprises a second pressure detector 70, in this embodiment an electronic pressure detector, which is disposed in the first flow channel 65 for detecting the pressure in the first flow channel 65.

The measurement device further comprises a flow meter 71, in this embodiment an electronic flow meter, which is disposed in the first flow channel 65, in this embodiment downstream of the second pressure detector 70, for detecting the flow rate in the first flow channel 65.

The measurement device further comprises a regulatable gas supply 72 which is fluidly connected to the first flow channel 65, in this embodiment upstream of the second pressure detector 70, for delivering a controlled gas flow through the first flow channel 65, and hence the nasal airway of a subject.

The measurement device further comprises a determination unit 75 which is operably coupled to the first and second pressure sensors 69, 70, the flow meter 71 and the gas supply unit 72.

The determination unit 75 comprises a calculation unit 77 for calculating the nasal resistance R from the pressure P detected by the second pressure sensor 69 and the flow rate F detected by the flow meter 71 for predetermined flow rates as developed by the gas supply unit 72. The pressure P and flow rate F are related to the nasal resistance R, which is the in series resistance of the inlet nasal cavity $R_{inlet}$ and the outlet nasal cavity $R_{outlet}$, by the equation $R=F/P$. The nasal resistance R is thus determined from the measured values of pressure P and flow rate F. In this embodiment the determination unit 75 is configured to enable calculation by the calculation unit 77 only on receipt of an output signal from the first pressure sensor 69; this signal being indicative that the subject is exhaling through the mouthpiece 63, which exhalation acts to close the oropharyngeal velum of the subject.

The determination unit 75 further comprises a display 79 for displaying the determined resistance values.

In an alternative embodiment the determination unit can include a communications port for communicating with a personal computer (PC) to allow downloading of the acquired data.

Operation of the delivery device will now be described hereinbelow.

A subject fits the nosepiece 61 to one nostril and grips the mouthpiece 63 in the mouth. The subject then exhales through the mouthpiece 63, which exhalation acts to close the oropharyngeal velum of the subject.

In one mode of use, in a single exhalation breath, the determination unit 75 actuates the gas supply unit 72 to deliver a gas flow having a predetermined flow rate, and determines the nasal resistance R for the detected values of pressure P and flow rate F, with the determined nasal resistance R being displayed on the display 79. In this mode, the nasal resistances R are determined for other flow rates F by repeated exhalation through the mouthpiece 63.

In another mode of operation, in a single exhalation breath, the determination unit 75 actuates the gas supply unit 72 successively to deliver a plurality of gas flows each having different predetermined flow rates, and determines the nasal resistance R for the detected values of pressure P and flow rate F, with the determined nasal resistance R being displayed on the display 79.

Finally, it will be understood that the present invention has been described in its preferred embodiments and can be modified in many different ways without departing from the scope of the invention as defined by the appended claims.

The invention claimed is:

1. A nasal delivery device for delivering at least one substance to a nasal cavity of a subject, including a delivery unit comprising:
    a nosepiece for fitting to a nostril of a subject;
    a mouthpiece through which the subject in use exhales to close the oropharyngeal velum;
    a breath analyzer configured to detect the concentration of at least one component in air exhaled during exhalation through the mouthpiece; and
    a substance supply unit for supplying at least one substance into the nasal cavity through the nosepiece during exhalation through the mouthpiece, the substance supply unit including a control unit configured to control the same to control supply of the at least one substance in response to the detected concentration.

2. The delivery device of claim 1, wherein the control unit is configured to actuate the substance supply unit to supply the at lease one substance at a predeterminable pressure.

3. The delivery device of claim 1, wherein the control unit is configured to actuate the substance supply unity to supply the at least one substance at a predeterminable flow rate.

4. The delivery device of claim 1, wherein the control unit is configured to actuate the substance supply unit to supply the at least one substance at one or both of a predeterminable pressure and a predeterminable flow rate.

5. The delivery device of claim 1, wherein the delivery unit further comprises:
    a flow channel fluidly connecting the nosepiece and the mouthpiece, whereby exhaled air from an exhalation breath is delivered through the nosepiece.

6. The delivery device of claim 5, wherein the substance supply unit includes a flow regulator for regulating the exhaled air flow.

7. The delivery device of claim 6, wherein the flow regulator is operably coupled to the control unit such as to allow for control of the same.

8. The delivery device of claim 1, wherein the delivery unit further comprises:
    a flow channel fluidly connected to the nosepiece through which a gas flow, separate to an exhaled air flow from an exhalation breath of a subject, is in use delivered; and
    a gas supply unit for supplying a gas flow to the flow channel.

9. The delivery device of claim 1, wherein the substance supply unit includes a dosing unit for supplying at least one substance.

10. The delivery device of claim 9, wherein the dosing unit comprises a nebulizer for supplying an aerosol.

11. The delivery device of claim 9, wherein the dosing unit comprises an aerosol canister for supplying an aerosol.

12. The delivery device of claim 9, wherein the dosing unit comprises a delivery pump unit for supplying an aerosol.

13. The delivery device of claim 12, wherein the dosing unit comprises a liquid pump unit for supplying a liquid aerosol.

14. The delivery device of claim 12, wherein the dosing unit comprises a powder pump unit for supplying a powder aerosol.

15. The delivery device of claim 9, wherein the dosing unit comprises a powder delivery unit for delivering a powder aerosol.

16. A nasal delivery device for delivering at least one substance to a nasal cavity of a subject, including a delivery unit comprising:
 a nosepiece for fitting to a nostril of a subject;
 a mouthpiece through which the subject in use exhales to close the oropharyngeal velum;
 a breath analyzer configured to detect the concentration of at least one component in air exhaled during exhalation through the mouthpiece;
 a substance supply unit for supplying at least one substance into the nasal cavity through the nosepiece during exhalation through the mouthpiece, the substance supply unit including a control unit configured to control the same to control supply of the at least one substance in response to the detected concentration; and
 an outlet unit comprising:
  a nosepiece for fitting in the other, outlet nostril of the subject; and
  an exit flow analyzer configured to analyze the concentration of at least one component in an air flow exiting the outlet nostril.

17. The delivery device of claim 16, wherein the exit flow analyzer is operably connected to the control unit, and the control unit is configured to control the substance supply unit in response to a concentration detected by the exit flow analyzer.

18. A method of delivering at least one substance to a nasal cavity of a subject, comprising the steps of:
 providing a delivery device including a delivery unit comprising a nosepiece for fitting to a nostril of subject, a mouthpiece through which the subject exhales, a breath analyzer configured to analyze the concentration of at least one component in exhaled air from an exhalation breath, and a substance supply unit for supplying at least one substance;
 actuating the substance supply unit to supply at least one substance; and controlling supply of the at least one substance by the substance supply unit in response to a concentration as detected by the breath analyzer.

19. The method of claim 18, wherein the step of actuating the substance supply unit comprises the step of:
 actuating the substance supply unit to supply the at least one substance at a predeterminable pressure.

20. The method of claim 18, wherein the step of actuating the substance supply unit comprises the step of:
 actuating the substance supply unit to supply the at least one substance at a predeterminable flow rate.

21. The method of claim 18, wherein the step of actuating the substance supply unit comprises the step of:
 actuating the substance supply unit to supply the at least one substance at one or both of a predeterminable pressure and a predeterminable flow rate.

22. The method of claim 18, wherein the delivery unit further comprises:
 a flow channel fluidly connecting the nosepiece and the mouthpiece, whereby exhaled air from an exhalation breath is delivered through the nosepiece.

23. The method of claim 22, further comprising the step of:
 regulating the exhaled air flow.

24. The method of claim 18, further comprising the step of:
 delivering a gas flow, separate to an exhaled air flow from an exhalation breath of a subject, through the nosepiece.

25. The method of claim 18, wherein the substance supply unit includes a dosing unit for supplying at least one substance.

26. The method of claim 25, wherein the dosing unit comprises a nebulizer for supplying an aerosol.

27. The method of claim 25, wherein the dosing unit comprises an aerosol canister for supplying an aerosol.

28. The method of claim 25, wherein the dosing unit comprises a delivery pump unit for supplying an aerosol.

29. The method of claim 28, wherein the dosing unit comprises a liquid pump unit for supplying a liquid aerosol.

30. The method of claim 28, wherein the dosing unit comprises a powder pump unit for supplying a powder aerosol.

31. The method of claim 25, wherein the dosing unit comprises a powder delivery unit for delivering a powder aerosol.

32. A method of delivering at least one substance to a nasal cavity of a subject, comprising the steps:
 providing a delivery device including a delivery unit comprising a nosepiece for fitting to a nostril of a subject, a mouthpiece through which the subject exhales, a breath analyzer configuration to analyze the concentration of at least one component in exhaled air from an exhalation breath, and a substance supply unit for supplying at least one substance;
 actuating the substance supply unit to supply at least one substance; and controlling supply of the at least one substance by the substance supply unit in response to a concentration as detected by the breathe analyzer;
 wherein the delivery device further includes an outlet unit comprising a nosepiece for fitting in the other, outlet nostril of the subject, and an exit flow configured to analyze the concentration of at least one component in an air flow exiting the outlet nostril.

33. The method of claim 32, further comprising the step of:
 controlling the substance supply unit in response to a concentration as detected by the exit flow analyzer.

34. The method of claim 33, wherein the step of controlling the substance supply unit in response to a concentration as detected by the exit flow analyzer comprises the step of:
 actuating the substance supply unit to supply further of the at least one substance in response to detection of a concentration of the at least one substance by the exit flow analyzer.

35. The method of claim 33, wherein the step of controlling the substance supply unit in response to a concentration as detected by the exit flow analyzer comprises the step of:
 actuating the substance supply unit to supply a reference substance; and
 controlling the substance supply unit in response to a concentration of the reference substance as detected by the exit flow analyzer.

36. The delivery device of claim 1, wherein the substance supply unit is operative to deliver a metered dose of the at least one substance, and the control unit is operative to meter delivery of the at least one substance in response to the detected concentration.

37. The method of claim 18, wherein the substance supply unit delivers a metered dose of the at least one substance, and the step of controlling supply of the at least one substance comprises metering delivery of the at least one substance in response to the detected concentration.

38. A nasal delivery device for delivering at least one substance to a nasal cavity of a subject, comprising:
   a first nosepiece for fitting to one, inlet nostril of a subject;
   a second nosepiece for fitting to the other, outlet nostril of the subject;
   a mouthpiece through which the subject in use exhales to close the oropharyngeal velum;
   an exit flow analyzer configured to analyze the concentration of at least one component in an air flow exiting the outlet nostril; and
   a substance supply unit for supplying at least one substance, the substance supply unit including a control unit configured to control the same to control supply of the at least one substance in response to a detected concentration.

39. The delivery device of claim 38, wherein the exit flow analyzer is operably connected to the control unit, and the control unit is configured to control the substance supply unit in response to a concentration detected by the exit flow analyzer.

40. A method of delivering at least one substance to a nasal cavity of a subject, comprising the steps of:
   providing a delivery device including a delivery unit comprising a first nosepiece for fitting to one, inlet nostril of a subject, a mouthpiece through which the subject exhales, and a substance supply unit for supplying at least one substance, and an outlet unit comprising a second nosepiece for fitting to the other, outlet nostril of the subject, and an exit flow analyzer configured to analyze the concentration of at least one component in an air flow exiting the outlet nostril;
   actuating the substance supply unit to supply at least one substance; and
   controlling supply of the at least one substance by the substance supply unit in response to a concentration as detected by the exit flow analyzer.

41. The method of claim 40, further comprising the step of:
   controlling the substance supply unit in response to a concentration as detected by the exit flow analyzer.

42. The method of claim 41, wherein the step of controlling the substance supply unit in response to a concentration as detected by the exit flow analyzer comprises the step of:
   actuating the substance supply unit to supply further of the at least one substance in response to detection of a concentration of the at least one substance by the exit flow analyzer.

43. The method of claim 41, wherein the step of controlling the substance supply unit in response to a concentration as detected by the exit flow analyzer comprises the step of:
   actuating the substance supply unit to supply a reference substance; and
   controlling the substance supply unit in response to a concentration of the reference substance as detected by the exit flow analyzer.

* * * * *